United States Patent [19]

Audeh et al.

[11] Patent Number: 4,822,938

[45] Date of Patent: Apr. 18, 1989

[54] PROCESSES FOR CONVERTING METHANE TO HIGHER MOLECULAR WEIGHT HYDROCARBONS VIA SULFUR-CONTAINING INTERMEDIATES

[75] Inventors: Costandi A. Audeh, Princeton; Weldon K. Bell, Pennington; Scott Han, Lawrenceville, all of N.J.; Robert E. Palermo, New Hope, Pa.

[73] Assignee: Mobil Oil Corporation, New York, N.Y.

[21] Appl. No.: 189,877

[22] Filed: May 3, 1988

[51] Int. Cl.$^4$ .............................................. C07C 1/00
[52] U.S. Cl. ...................... 585/324; 568/69; 585/310; 585/319; 585/408; 585/638; 585/733; 585/943
[58] Field of Search ............... 585/310, 319, 324, 408, 585/638, 733, 943; 568/69

[56] References Cited

U.S. PATENT DOCUMENTS

| | | | |
|---|---|---|---|
| 2,468,904 | 5/1949 | Wagner | 23/206 |
| 2,565,195 | 8/1951 | Bell | 260/609 |
| 3,894,105 | 7/1975 | Chang et al. | 260/668 R |
| 4,265,735 | 5/1981 | Audeh et al. | 208/234 |
| 4,373,109 | 2/1983 | Olah | 585/638 |
| 4,480,143 | 10/1984 | Chang et al. | 585/469 |
| 4,543,434 | 9/1985 | Chang | 585/310 |
| 4,618,723 | 10/1986 | Herrington et al. | 585/638 |
| 4,618,732 | 10/1986 | Gesser et al. | 568/910.5 |

OTHER PUBLICATIONS

Kirk–Othmer Encyclopedia of Chemical Technology, Third Ed., vol. 4, 1978, pp. 747–749.

*Primary Examiner*—Curtis R. Davis
*Attorney, Agent, or Firm*—Alexander J. McKillop; Charles J. Speciale; Edward F. Kenehan, Jr.

[57] ABSTRACT

There is provided a process for converting methane to higher molecular weight hydrocarbons. In a first step, methane is contacted with elemental sulfur under conditions sufficient to produce carbon disulfide. Carbon disulfide from this step is then contacted with methane and hydrogen under conditions sufficient to convert methane and to produce $CH_3SH$. This $CH_3SH$ is then contacted with a sufficient catalyst, such as a zeolite, especially ZSM-5, under conditions sufficient to produce hydrocarbons having two or more carbon atoms.

11 Claims, No Drawings

PROCESSES FOR CONVERTING METHANE TO HIGHER MOLECULAR WEIGHT HYDROCARBONS VIA SULFUR-CONTAINING INTERMEDIATES

BACKGROUND

This application relates to processes for converting methane to higher molecular weight hydrocarbons, wherein methane is initially reacted with elemental sulfur to produce sulfur-containing intermediates which are, in turn, converted to hydrocarbons having two or more carbon atoms.

Natural gas is abundently available and provides a power source as a combustible fuel. However, the use of natural gas as fuel is often inconvenient for reasons of storage and handling. Accordingly, it would be desirable to convert components of natural gas to more valuable hydrocarbons. For example, conversion of natural gas to a liquid fuel would obviate certain problems of storage and handling. The main component of natural gas is methane.

The Chang U.S. Pat. No. 4,543,434 describes, inter alia, a process for converting methane by the following steps:

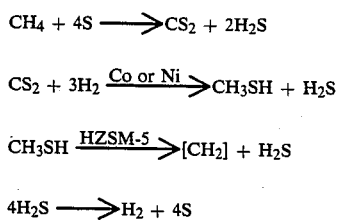

where $[CH_2]$ represents one or more hydrocarbons having at least two carbon atoms. The entire disclosure of this Chang U.S. Pat. No. 4,534,434 is expressly incorporated herein by reference.

SUMMARY

According to an aspect of this application, there is provided a process for converting methane to higher molecular weight hydrocarbons, said process comprising the steps of:
(i) contacting methane with sulfur under conditions sufficient to generate carbon disulfate;
(ii) contacting said carbon disulfide of step (i) with methane and hydrogen under conditions sufficient to generate $CH_3SH$, whereby methane is converted along with carbon disulide in this step (ii); and
(iii) contacting said $CH_3SH$ of step (ii) with a sufficient catalyst under conditions sufficient to produce hydrogen sulfide and a mixture of hydrocarbons having at least two carbon atoms.

EMBODIMENTS

In accordance with an aspect of the present application, carbon disulfide is generated by reacting methane with elemental sulfur. This carbon disulfide generation may take place by the process of Folkner et al as disclosed at I & EC, 2202, 1950. The Folkins process may also be used to produce carbon disulfide. This Folkins process is disclosed at pages 747-749 of the *Kirk-Othmer Encyclopedia of Chemical Technology*, Third Edition, Vol. 4, 1978. In accordance with this Folkins process, methane is preheated and mixed with vaporized sulfur and this mixture is reacted at about 580°-635° C. at a pressure of about 2.5-5 atmospheres in an adiabatic reactor. In this Folkins process an excess of sulfur (e.g. 10-15% excess) is used with respect to methane. The overall stoichiometry of this reaction is $CH_4 + 4S \rightarrow CS_2 + 2H_2S$.

Other processes for producing carbon disulfide by reacting methane and sulfur are described in the Wagner U.S. Pat. No. 2,468,904, the entire disclosure of which is expressly incorporated herein by reference. This passage extending from line 31 to line 37 on column 1 of this Wagner patent is particularly noted.

Whenever sulfur is used in sufficient quantities, e.g., in excess to methane as per the above-mentioned reaction, essentially all of the hydrogen from the methane which is reacted goes to form hydrogen sulfide as a product. However, when a stoichiometric deficiency of sulfur is present, hydrogen from methane may go to form elemental hydrogen (i.e. $H_2$) as well as hydrogen sulfide. Accordingly, in a methane rich mode the hydrogen content of the product can be maximized. Preferably for the reaction to produce a hydrogen rich product, the number of moles of S with respect to that of $CH_4$ should be less than 0.5, preferably less than about 0.2. Thus, if it is assumed that sulfur exists in the $S_8$ form, then the mole ratio should be at least $40CH_4:1S_8$, however, if the sulfur is assumed to exist in the form of $S_2$, then this mole ratio becomes $10CH_4:1S_2$.

In general, a $S_x - 1CH_4 = ax$ when ax is 0.5, preferably 0.2. The effect of $[aS_x]/[1CH_4] = ax$ on the production of hydrogen and $H_2S$ in Step 1 is illustrated in Table 1.

TABLE 1

| ax | [H$_2$/H$_2$S] | |
|---|---|---|
| | 650° C. | 750° C. |
| 0.05 | 4 | 14 |
| 0.1 | 2 | 6 |
| 0.2 | 1 | 3 |

Examples of conditions which can be used to produce carbon disulfide from methane and sulfur in the hydrogen rich product mode include a temperature of from about 550° C. to about 900° C. and a pressure of from about 1 atmosphere to about 5 atmospheres, e.g., from about 1 atmosphere to about 2 atmospheres.

When hydrogen is coproduced with hydrogen sulfide, the $H_2S$ may be separated by any known process, such as those processes exemplified in Chemical and Process Technology Encyclopedia, McGraw-Hill, 1974, pp 12-15. Hydrogen produced in this step (i) may be used as a reactant in step (ii) along with unreacted methane and carbon disulfide from step (i). It is not necessary to completely remove hydrogen sulfide from the product of step (i), and at least a portion of this hydrogen sulfide may be carried over with the carbon disulfide reactant of step (ii).

Sulfur can be generated from hydrogen sulfide by the Claus process, wherein hydrogen sulfide is reacted with oxygen in the presence of alumina in accordance with the following reaction:

$$2H_2S + O_2 \xrightarrow{Al_2O_3} 2S + 2H_2O$$

Sulfur may also be obtained by the following reaction sequence:

$$2H_2S + 2(n/2M) \rightarrow 2M_{n/2}S + 2H_2$$

$$2M_{n/2}S \rightarrow 2(n/2M) + 2S$$

where M represents a suitable metal, e.g., a Group VIII or VIB metal. Examples of M include Fe, Co, Ni, Bi and Mo. This latter two-step reaction sequence for producing S is disclosed in the Chang U.S. Pat. No. 4,543,434. The reaction of hydrogen sulfide with metal may take place at temperatures between 0°-300° C. and at pressures between 0-2000 psig. The reaction of metal sulfide to regenerate metal and sulfur may take place at a temperature of from about 250° C. to about 1100° C. The sulfur produced may be recycled into the first reaction step, wherein methane is reacted with sulfur.

After carbon disulfide is generated it may be contacted with methane and hydrogen under conditions sufficient to generate $CH_3SH$, whereby methane is converted along with carbon disulfide. The overall stoichiometry of this reaction may be as follows:

$$CH_4 + CS_2 + 2H_2 \rightarrow 2CH_3SH$$

Without being bound by any particular theory or mode of reaction, it is theorized that this overall reaction could possibly take place in two-steps as follows:

$$CS_2 + 2H_2 \rightarrow CH_3SH + S$$

$$S + CH_4 \rightarrow CH_3SH$$

The following table presents thermodynamic calculations for the present methane conversion, wherein methane is reacted along with the carbon disulfide and hydrogen, as a function of the temperature and pressure of the reaction:

|     | % METHANE CONVERTED ATM | | |
| --- | --- | --- | --- |
| K   | 1   | 10  | 100 |
| 700 | 1   | 7   | 38  |
| 600 | 3   | 22  | 63  |
| 500 | 16  | 56  | 85  |
| 400 | 65  | 88  | 96  |

Examples of conditions for reacting methane with hydrogen and carbon disulfide include a temperature of from about 25° C. to about 500° C. and a pressure of from about 1 atmosphere to about 200 atmosphere.

Whenever methane is used as a reactant as described herein, it may be used in pure form or essentially pure form in admixture with trace amounts of impurities. The methane may also be reacted in the presence of other inert or reactive gasses. For example, natural gas may be used as a source of methane reactant.

The reaction of methane with carbon disulfide and hydrogen may take place in the presence or absence of hydrogen sulfide. When present in this reaction, the hydrogen sulfide may also react with methane and/or carbon disulfide under certain conditions. In addition to $CH_3SH$, other organosulfur compounds, such as $(CH_3)_2S$, may be coproduced in the reaction of methane with carbon disulfide and hydrogen.

Organosulfur compounds, such as $CH_3SH$ and $(CH_3)_2S$, may be contacted with a sufficient catalyst under condition sufficient to produce hydrogen sulfide and a mixture of hydrocarbons having at least two carbon atoms. Examples of such reactions are described in the aforementioned Chang U.S. Pat. No. 4,543,434 and in the Audeh et al U.S. Pat. No. 4,265,735, the entire disclosure of which is expressly incorporated herein by reference. Similar reactions involving the production of gasoline are also described in U.S. Pat. Nos. 3,894,102 and 3,894,103, the entire disclosures of which are expressly incorporated herein by reference.

A preferred catalyst for converting organosulfur compounds to hydrocarbons, e.g., gasoline, is ZSM-5. However, other zeolites, such as those having a Constraint Index of from 1 to 12, may also be particularly useful.

The members of a particular class of zeolites useful for converting organosulfur compounds have an effective pore size of generally from about 5 to about 8 Angstroms, such as to freely sorb normal hexane. In addition, the structure provides constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the particular class. Windows of 10-membered rings are preferred, although, in some instances, excessive puckering of the rings or pore blockage may render these zeolite ineffective.

Although 12-membered rings in theory would not offer the same amount of constraint as 10-membered rings, it is noted that the puckered 12-ring structure of TMA offretite does show some constrained access. Other 12-ring structures may exist which may be particularly useful.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g., less than 5 Angstroms. On the other hand, zeolites which provide relatively free access to the internal zeolite structure have a low value for the Constraint Index, and usually pores of large size, e.g., greater than 8 Angstroms. The method by which Constraint Index is determined is described fully in U.S. Pat. No. 4,016,218, incorporated herein by reference for details of the method.

Constraint Index (CI) values for some typical materials are:

|         | CI (at test temperature) |
| ---     | ---                      |
| ZSM-4   | 0.5 (316° C.)            |
| ZSM-5   | 6-8.3 (371° C.-316° C.)  |
| ZSM-11  | 5-8.7 (371° C.-316° C.)  |
| ZSM-12  | 2.3 (316° C.)            |
| ZSM-20  | 0.5 (371° C.)            |
| ZSM-22  | 7.3 (427° C.)            |
| ZSM-23  | 9.1 (427° C.)            |
| ZSM-34  | 50 (371° C.)             |
| ZSM-35  | 4.5 (454° C.)            |
| ZSM-48  | 3.5 (538° C.)            |
| ZSM-50  | 2.1 (427° C.)            |

| | CI (at test temperature) |
|---|---|
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index provides a means for identifying those zeolites which are useful in the present organosulfur conversion. The very nature of this parameter and the recited technique by which it is determined, however, admit of the possiblity that a given zeolite can be tested under somewhat different conditions and thereby exhibit different Constraint Indices. Constraint Index seems to vary somewhat with severity of operations (conversion) and the presence or absence of binders. Likewise, over variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a useful means for characterizing the zeolites of particular interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein within the approximate range of 1 to 12.

In addition to the above-mentioned zeolites other suitable catalysts for converting organosulfur compounds to hydrocarbons may include certain amorphous materials and other crystalline materials, particularly catalytically active molecular sieve materials, such as SAPO materials, as described in the Lok et al U.S. Pat. No. 4,440,871, the entire disclosure of which is expressly incorporated herein by reference. Especially when ZSM-5 is employed as the active component of the catalyst, the conversion of organosulfur compounds to hydrocarbons and hydrogen sulfide may take place at a temperature of from about 200° C. to about 650° C. and at a pressure of from about 0 to about 2000 psig.

It is noted that certain of the reactions mentioned hereinabove generate hydrogen in the product. These reactions include the reaction of methane with a stoichiometric deficiency of sulfur and the reaction of hydrogen sulfide with metal. This hydrogen may be recovered and used as a reactant in the reaction of methane along with carbon disulfide and hydrogen. A methane reformer may also be used to generate hydrogen reactant in accordance with the following reaction:

$$CH_4 + H_2O \rightarrow CO_2 + H_2.$$

What is claimed is:

1. A process for converting methane to higher molecular weight hydrocarbons, said process comprising the steps of:
   (i) contacting methane with sulfur under conditions sufficient to generate carbon disulfide;
   (ii) contacting said carbon disulfide of step (i) with methane and hydrogen under conditions sufficient to generate $CH_3SH$, whereby methane is converted along with carbon disulfide in this step (ii), and
   (iii) contacting said $CH_3SH$ of step (ii) with a sufficient catalyst under conditions sufficient to produce hydrogen sulfide and a mixture of hydrocarbons having at least two carbon atoms.

2. A process according to claim 1, wherein the reaction mixture of step (i) comprises an excess of methane in relation to sulfur, whereby a portion of the methane is converted into elemental hydrogen along with carbon disulfide and hydrogen sulfide, such that carbon disulfide is produced in admixture with $H_2$, $H_2S$ and unreacted methane.

3. A process according to claim 2, wherein hydrogen generated in step (i) is used as a source of hydrogen in step (ii).

4. A process according to claim 2, wherein the ratio of the number of moles of S to the number of moles of $CH_4$ in the reaction mixture of step (i) is 0.5 or less.

5. A process according to claim 2, wherein the ratio of the number of moles of S to the number of moles of $CH_4$ in the reaction mixture of step (i) is 0.2 or less.

6. A process according to claim 4, wherein the molar ratio of $H_2$ is $H_2S$ produced in step (i) is 1 or more.

7. A process according to claim 4, wherein the molar ratio of $H_2$ to $H_2S$ produced in step (i) is 4 or more.

8. A process according to claim 2, wherein $(CH_3)_2S$ is coproduced along with $CH_3SH$ in step (ii) and said $(CH_3)_2S$ is contacted with a sufficient catalyst under conditions sufficient to produce hydrogen sulfide and a mixture of hydrocarbons having at least two carbon atoms.

9. A process according to claim 1, wherein the reaction mixture of step (i) comprises a sufficient amount of sulfur to convert all of the methane in the reaction mixture, whereby essentially all of the hydrogen in the methane reactant is converted to $H_2S$.

10. A process according to claim 9, wherein the carbon disulfide is produced in step (i) in accordance with the stoichiometry set forth in the following reaction:

$$CH_4 + 4S \rightarrow CS_2 + 2H_2S.$$

11. A process according to claim 9, wherein $CH_3SH$ is produced in step (ii) in accordance with the stoichiometry set forth in the following reaction:

$$CH_4 + CS_2 + 2H_2 \rightarrow 2CH_3SH.$$

* * * * *